(12) United States Patent
Clark (10) Patent No.: US 10,274,565 B2
(45) Date of Patent: Apr. 30, 2019

(54) MAGNETIC RESONANCE IMAGING (71) Applicant: MAGNEPATH PTY LTD, Brentwood (AU)

(72) Inventor: Paul Clark, Brentwood (AU)

(73) Assignee: MagnePath Pty Ltd, Brentwood (AU)

( * ) Notice: Subject to any disclaimer, the term of this patent is extended or adjusted under 35 U.S.C. 154(b) by 892 days.

(21) Appl. No.: 14/726,375

(22) Filed: May 29, 2015

(65) Prior Publication Data
US 2015/0285883 A1 Oct. 8, 2015

Related U.S. Application Data (63) Continuation of application No. PCT/AU2013/001379, filed on Nov. 27, 2013.

(30) Foreign Application Priority Data

Nov. 30, 2012 (AU) .............................. 20192905226

(51) Int. Cl.
*G01R 33/48* (2006.01)
*A61B 5/055* (2006.01)
(Continued)

(52) U.S. Cl.
CPC .......... *G01R 33/4828* (2013.01); *A61B 5/055* (2013.01); *G01R 33/5615* (2013.01); *G01R 33/58* (2013.01); *A61B 5/4869* (2013.01)

(58) Field of Classification Search
CPC .............. G01R 33/4828; G01R 33/055; G01R 33/4869; G01R 33/5615; G01R 33/58
See application file for complete search history.

(56) References Cited

U.S. PATENT DOCUMENTS 7,689,265 B2 * 3/2010 Shen ........................ G06K 9/38
    382/128
8,027,713 B2 * 9/2011 Yatsui .............. G01R 33/56563
    324/307

(Continued)

FOREIGN PATENT DOCUMENTS

| JP | 2005-218505 | 8/2005 |
| KR | 10-2011-0083868 | 7/2011 |
| WO | WO 2012/038886 | 3/2012 |

OTHER PUBLICATIONS

Yu et al., "Multiecho Water-Fat Separation and Simultaneous R*$_2$ Estimation With Multifrequency Fat Sepctrum Modeling," Magnetic Resonance in Medicine 60:1122-1134 (2008).

(Continued)

*Primary Examiner* — Dixomara Vargas
(74) *Attorney, Agent, or Firm* — Levine Bagade Han LLP (57) ABSTRACT

A method of characterising relative proportions of magnetic resonance (MR) chemical species where one or more of the chemical species has a multi-peak MR spectra includes defining an in-phase measurement time window and an out-phase measurement time window relative to a frequency difference between the two dominant spectral peaks of at least one said multi-peak chemical species. The in-phase window captures the signal that is progressing to being maximally in-phase for the two dominant peaks, and the out-phase window captures the signal that is progressing to being maximally out of phase for the two dominant peaks. The method includes identifying an increased upward deviation in the signal over the in-phase window relative to a reference signal decay over the out-phase window, where such upward deviation in the signal over the in-phase window provides an indicator of the increased presence of the one or more multi peak spectral species over the other species.

23 Claims, 5 Drawing Sheets

(51) Int. Cl.
   *G01R 33/561* (2006.01)
   *G01R 33/58* (2006.01)
   *A61B 5/00* (2006.01)

(56) References Cited

U.S. PATENT DOCUMENTS

| | | | |
|---|---|---|---|
| 2007/0165923 A1* | 7/2007 | Shen | G06K 9/38 |
| | | | 382/128 |
| 2007/0247153 A1 | 10/2007 | Yu et al. | |
| 2009/0131796 A1* | 5/2009 | Shen | A61B 8/14 |
| | | | 600/445 |
| 2011/0267054 A1 | 11/2011 | He et al. | |
| 2012/0301007 A1 | 11/2012 | Shirai et al. | |
| 2016/0071263 A1* | 3/2016 | Thiruvenkadam | G06T 7/136 |
| | | | 382/131 |
| 2016/0216352 A1* | 7/2016 | Eggers | G01R 33/4828 |

OTHER PUBLICATIONS

Yu et al., "Robust Multipoint Water-Fat Separation Using Fat Likelihood Analysis," Magnetic Resonance in Medicine 67:1065-1076 (2012).

\* cited by examiner

MAGNETIC RESONANCE IMAGING

CROSS-REFERENCE TO RELATED APPLICATIONS

This application is a continuation of International Application No. PCT/AU2013/001379, filed 27 Nov. 2013, which claims priority to Australian Application No. 2012905226, filed 30 Nov. 2012, both of which are incorporated by reference herein in their entireties.

FIELD OF THE INVENTION

The present invention relates to magnetic resonance imaging.

BACKGROUND

Clinical magnetic resonance (MR) imaging techniques typically detect a signal from hydrogen protons.

The detected hydrogen protons are predominantly part of water, or part of organic molecules such as proteins, carbohydrates, and fat, or part of introduced inorganic-organic complexes, such as silicone.

The respective signal intensities of the various hydrogen proton pools in an imaging voxel results from a combination of their spin density, longitudinal and transverse, relaxation time (T1 and T2, respectively), and the parameters of the imaging sequence used.

By exploiting the particular characteristics of hydrogen atoms (hydrogen having a single proton (1H) nucleus), MR imaging (MRI) provides good contrast between soft tissues, according to the chemical form and local microscopic environment of the hydrogen containing species in the tissues, such as silicone or lipid (fat) molecules.

The electronic shielding of the hydrogen protons in macromolecules such as fat or silicone is greater than that experienced by hydrogen protons in water. This results in different microscopic magnetic field environments for the hydrogen protons, and subsequently different hydrogen proton resonant frequencies for the different hydrogen-containing chemical species—referred to as chemical shift.

For example, fat is known to have a complex spectrum with multiple peaks owing to its various hydrogen proton chains, for which the largest peak is shifted downfield by ≈3.5 ppm from the peak for water.

A known MR imaging modality relies on suppression of the fat peak compared to the water peak. A more advanced approach for fat suppression relative to the water peak is to excite the water peak directly via spatial spectral pulses, rather than suppress the fat peak.

Chemical shift-based water-fat separation methods that successfully and accurately separate the signals from water and fat provides a mechanism by which the fatty infiltration of organs can be quantified in a variety of disease conditions. For example, non-alcoholic fatty liver disease (NAFLD) is a major cause of chronic liver disease in the USA, affecting approximately one third of the US population. The current benchmark for the diagnosis of NAFLD is liver biopsy, which is expensive, risky, and suffers from high sampling variability, greatly limiting its clinical utility. Therefore, there is a great need for noninvasive biomarkers such as imaging, not only for early detection of disease, but also to reliably quantify the severity of disease.

In the case where two distinct MR chemical species can dominate the MR signal within a given volume, it can be highly problematic to ascribe a given signal component to a given species, unless the relative proportions or average rate at which the signal decays or recovers for a given species is known relative to the other species a priori, or other anatomical reference information is available to make the distinction. This is classically seen in spin-echo imaging where multi-exponential decay curve fitting, is attempted on signal intensity data collected at different echo times to derive the characteristic transverse relaxation rates and relative proportions of two or more MR species contributing to the MR signal. A similar situation arises in gradient-echo imaging where a sinusoidal oscillation is superimposed on the MR signal decay curve owing to differences in the characteristic MR frequencies of the chemical species contributing to the MR signal. An example of this occurs in the gradient-echo imaging of a volume containing both water and fat, where it is desired to isolate the water and fat signals and/or determine the relative percentage contributions of each. When a water/fat signal model assumes a characteristic MR frequency for each species and is being fit to magnitude image data, then assignment of a given signal component to either water or fat cannot be reliably performed, unless it is known that a given tissue cannot exceed 50% fat, or other anatomical information can be used to make the distinction.

The water/fat ambiguity problem that arises in the fitting of a bi-exponential signal decay model to gradient-echo image data arises from over-simplification of the model where fat is characterised by a single resonant frequency. The ambiguity has the potential for being resolved by using a multi-peak spectral model for fat instead that accounts for contributions to the MR signal from the major hydrogen proton groups on the fat molecule, but utility beyond the 50% fat fraction has not been demonstrated by magnitude-based techniques employing this approach (Yokoo et al in 2011).

The use of complex data with both magnitude and phase can help overcome the water/fat ambiguity problem, but also requires the determination of a field map, with complex data being further sensitive to phase errors from various sources (Yu et al in 2008, Reeder et al in 2009, US patent application published as US 2011/0254547 to Reeder et al).

However, ambiguity can still arise if the initial estimates for the relative proportions of fat and water and their relaxation rates more closely reflect the actual values for the other species, as the fit is then likely to converge to an incorrect assignment of each component. This result can easily arise in bi-exponential signal decay modelling, where there are many local minima for the mean square error of the difference between the fit and the data, to which the fitting routine may be drawn as representing the global minimum solution, and thus falsely ascribe the fat component as the water component, and vice-versa.

Regarding water-silicone separation MR imaging techniques, it will be appreciated that using one or more forms of the present invention enables the presence of a silicone rich species to be assessed, thereby identifying whether leakage or damage of an implant has occurred. This can provide a vitally important non-invasive safety screening technique for breast and other silicone based implants.

It is desirable of the present invention to provide a magnetic resonance technique that enables chemical separation by quantifying the proportion of one selected species, such as fat or silicone, from water in tissue.

SUMMARY OF THE INVENTION

With the aforementioned in view, an aspect of the present invention provides a method of characterizing relative proportions of magnetic resonance (MR) chemical species where one or more of the chemical species has a multi-peak MR spectra, the method including:

A) defining an in-phase measurement time window and an out-phase measurement time window relative to a frequency difference between the two dominant spectral peaks of at least one said multi-peak chemical species, where the in-phase window captures signal that is progressing to being maximally in-phase for the two dominant peaks, and the out-phase window captures signal that is progressing to being maximally out of phase for the two dominant peaks, and B) identifying an increased upward deviation in the signal over the in-phase window relative to a reference signal decay over the out-phase window, where such upward deviation in the signal over the in-phase window provides an indicator of the increased presence of the one or more multi peak spectral species over the other species.

The method may be expanded to including identifying deviation in signal over the out-phase window relative to the reference signal decay over the out-phase window, where such out-phase deviation acts as an indicator of the reduced presence of the one or more multi-peak spectral species relative to the other species.

One or more forms of the present invention advantageously enables MR imaging of the multi peak chemical species.

Preferably the multi peak chemical species is fat or silicone.

The proportion and distribution of fat in a body, such as visceral and/or sub-cutaneous fat, or within an organ or tissue, such as the liver, may be MR imaged using one or more embodiments of the present invention.

The reference signal decay may be taken to be representative of averaging the relaxation affects of the chemical species contributing to the MR signal, such that it may be further represented by a single exponential decay.

As the percentage of the multi peak chemical species increases, deviation from this reference decay increases. Thus, it then becomes possible to derive initial estimates for two or more chemical species (e.g. water and fat) fractions that are not inadvertently swapped, e.g. 25% fat and 75% water relative to 75% fat and 25% water. A 75% fat content will contribute to an increased upward deviation in the measured signal in the in-phase window compared to a 25% fat content.

One or more embodiments of the present invention beneficially enables the characterization of magnetic resonance (MR) relaxation rates and relative proportions of two different magnetic resonant chemical species, where one chemical species has two or more dominant MR spectral peaks (such as the 1H MR spectra of fat) relative to the other chemical species that has one dominant MR spectral peak (such as for the 1H MR spectra of water).

Accordingly, the present invention advantageously enables imaging of the percentage/proportion amount of fat (or other selected species) and water in tissues.

It will be appreciated that the present invention can be employed to identify other multi-spectral species relative to water. For example, silicone, to identify and quantify the leakage of silicone from implants into or adjacent tissues.

There is inherent difficulty in isolating the proportions of magnetic resonant chemical species contributing to the MR signal behaviour within tissues in 1H (hydrogen proton) clinical imaging, be that for the average signal over a region of interest, or the signal ascribed to an individual voxel. This is owing to the fact that the MR relaxation or recovery in signal for any given hydrogen proton pool within a signal volume (e.g.; voxel) typically follows the same form of signal evolution curve as any other hydrogen proton pool. When there are two dominant hydrogen proton pools, it is then difficult to not inadvertently mis-assign the proportions of each pool.

The present invention overcomes the problem of mis-assigning and/or sufficiently refining the initial estimates of the fat and water components through analysis of the behaviour between two peaks of a multi-peak spectral model for the target chemical species, such as fat, with respect to the single (water) resonant peak.

It will be apparent to those skilled in the relevant arts that the invention can also be applied to the separation of other than 1H MR chemical species, such as for example water from silicone.

It will be further apparent to those skilled in the relevant art that the estimate of the percentage fat fraction can be further refined to take into account other potential confounds, such as R2* enhancement, the extent of which can also be estimated from the echo time image data collected.

Other derivations based on information obtained within the concept of in-phase and out-phase windows may also be determined that fall within the scope of this invention.

The concept of defining an in-phase window and out-phase window relative to the frequency difference of the two main fat spectral peaks is considered profound. In a signal volume containing water and fat, increases in percentage fat content will lead to increased upward deviation of the measured signal in the in-phase window relative to a reference signal decay, optimally expressed as a single exponential decay that is an average representation of the relaxation contributions from water and fat. As the percentage of fat content increases, deviation from this reference decay increases. It then becomes possible to derive initial estimates for the water and fat fractions that are not inadvertently swapped, as for say 25% fat and 75% water relative to 75% fat and 25% water. A 75% fat content will contribute to an increased upward deviation in the measured signal in the in-phase window compared to a 25% fat content.

A further embodiment of the present invention includes determining reference signal decay by an empirical approach including the steps of: fractioning the out-phase window into two smaller windows, determining an average intensity value and an average measurement time value in each of the smaller windows, and using the two average intensity/measurement time pairs to determine a 2-point approximation for the reference relaxation process according to the equation of single exponential decay.

Preferably the deviation in signal intensity may be determined from the reference signal decay by subtracting the reference signal intensity calculated from the reference relaxation equation at a given measurement time from the actual signal intensity at that measurement time, normalised relative to that actual signal intensity.

Characteristic in-phase or out-phase deviation may be determined from the in-phase or out-phase deviations, respectively. Preferably, a characteristic in-phase or out-phase deviation may be determined as the greatest absolute deviation over the in-phase or out-phase window, respectively.

A method of the present invention may include determining the proportion of a multi-peak chemical species by a combination of scaling and thresholding of the in-phase and out-phase deviations.

A lesser proportion of the multi-peak chemical species relative to the other species may be taken to be equal to the scaled out-phase deviation within empirically determined thresholds for the in-phase and out-phase deviations.

A greater proportion of the multi-peak chemical species relative to the other species may be taken to be equal to a scaling of one minus the scaled out-phase deviation outside of empirically determined thresholds for the in-phase and out-phase deviations.

One or more embodiments of the present invention may use the proportion of the multi-peak chemical species to determine initial estimates of the signal intensities of the chemical species at a zero measurement time with reference to the signal intensity at a zero measurement time from the reference signal decay.

Preferably, one or more embodiments of the present invention includes characterizing magnetic resonance (MR) relaxation rates and relative proportions of the two or more magnetic resonant chemical species, where one said chemical species has two or more dominant MR spectral peaks relative to the other said chemical species that has one dominant MR spectral peak.

One or more embodiments of the present invention may include characterizing magnetic resonance (MR) relaxation rates and relative proportions of the two or more magnetic resonant chemical species, where one said chemical species has two or more dominant MR spectral peaks relative to the other said chemical species that has one dominant MR spectral peak.

Preferably, the chemical species with two or more dominant spectral peaks is fat and the chemical species with one dominant spectral peak is water.

A percentage or proportion of fat fraction may be estimated, preferably including accounting for one or more additional confounds from collected echo time image data. One or more additional confounds may include $R2^*$ enhancement.

Preferably, gradient-echo image data may be collected out to echo times where either complex signals from the two chemical species are next in-phase after having first been out of phase, or to where complex signals for two dominant hydrogen proton pools of the species with a multi-peak spectra are next in phase having been first out of phase, whichever is the longer.

The relative proportions of the two or more chemical species may be estimated by separating collected data out to the longest echo time into two measurement time windows.

A first measurement time window may extend out from an echo time of 0 ms to an echo time point where the complex signals from the two dominant fat hydrogen proton pools are first out of phase.

A second measurement time window may cover a span of echo times where the complex signal from the two dominant fat hydrogen proton pools are coming back in phase.

BRIEF DESCRIPTION OF THE DRAWINGS

One or more embodiments of the present invention will hereinafter be described with reference to the accompanying drawings, in which.

DETAILED DESCRIPTION

Figure 1:
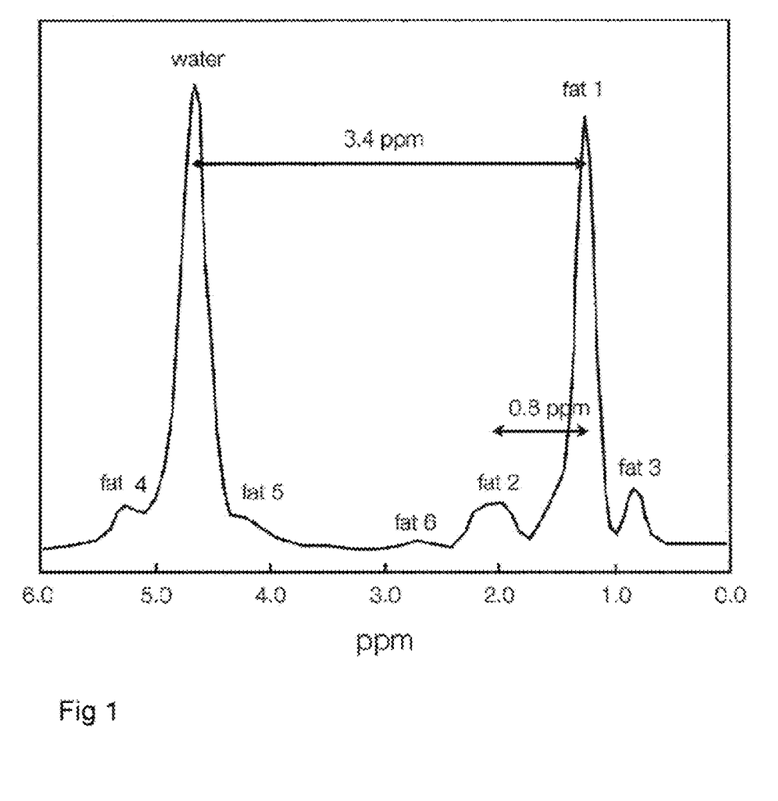
FIG. 1 shows a graph of magnetic resonance (MR) spectra (spectral diagram) revealing the separation in peaks for water and fat.

Referring to FIG. 1, a fat MR spectrum is shown with multiple peaks 1-6, with the dominant (fat 1) peak separated 3.4 ppm from a dominant water peak. The fat 2 secondary peak is separated 0.8 ppm from the dominant fat 1 peak.

Figure 2:
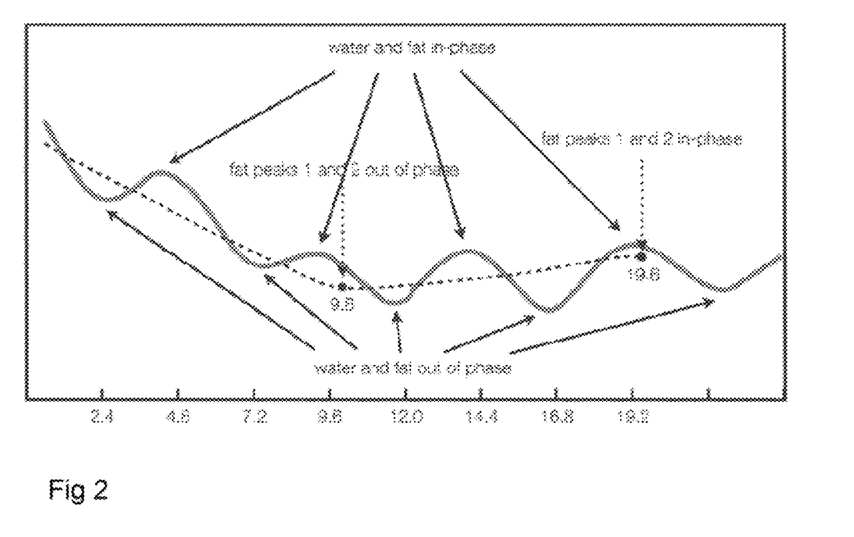
FIG. 2 shows a gradient echo decay indicating the in-phase and out-phase oscillation for water and fat.

A gradient echo decay graph is shown in FIG. 2 for a field strength of 1.5 T. A decay line shows as a sinusoidal oscillation between water and fat in-phase maxima and water and fat out-phase minima. The dominant fat 1 and secondary fat 2 in-phase maximum is shown at 19.6 ms, and the out-phase minimum at 9.8 ms.

Figure 3:
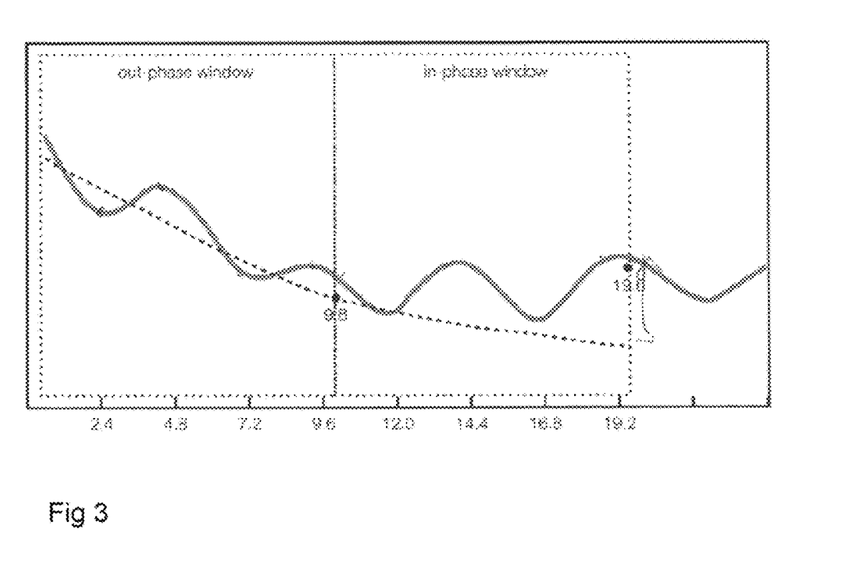
FIG. 3 shows specific in-phase and out-phase windows from the gradient echo decay trace of FIG. 2.

FIG. 3 identifies the respective out-phase and in-phase windows. Thus, when the difference between the water-fat resonance decay signal and reference signal decay increases there is an increased proportion of fat.

In a test scan, magnitude gradient echo image data was acquired on phantoms and volunteers at 1.5 T and 3.0 T (Siemens Avanto and Philips Achieva, respectively), with a maximum scan time of 30 s. Test phantoms included yogurt, cream, butter, lard, and sausages, for which the percentage fat content was obtained from the nutritional information on the product labels. In each case, a 2-D multi-echo spoiled gradient echo sequence was run with the following parameters: flip angle 20° and TR 200 ms to reduce T1-weighting; 8 equally spaced echo times per field strength of 3.6 ms.T, slice thickness 8 mm; bandwidth of 500 Hz/pixel (at 1.5 T) and 1970 Hz/pixel (at 3.0 T); matrix size 256 pixels.

Fat-water signal decay models were then implemented utilizing an embodiment of the present invention for multi component MR parameter mapping In one particular test, a magnitude-based gradient echo image technique for 0 to 100% fat-water separation with dual $R2^*$ mapping was conducted. A multi-peak spectral model for fat was implemented with five frequency components of 243 Hz, 217 Hz, 166 Hz, 32 Hz, and −38 Hz (per 1.5 T) relative to water, with corresponding normalised weights of 0.09, 0.7, 0.12, 0.04, and 0.05, as reported in the literature. Separate $R2^*$ parameters were modelled for water and fat. Non-linear curve fitting was performed pixel-by-pixel to signal power as a function of echo time using a simplex simulated annealing technique. The non-zero baseline of the magnitude image data, determined from an automated background noise analysis, was subtracted in quadrature from the pixel signal intensities prior to fitting. Initial estimates for the fat and water signal proportions were calculated from an embodiment of this invention. The fitted signal fractions were converted to volume fractions to provide percentage fat concentrations. Accuracy and precision were calculated as the mean and standard deviation of the differences between the calculated and labelled fat concentrations.

Figure 4A:
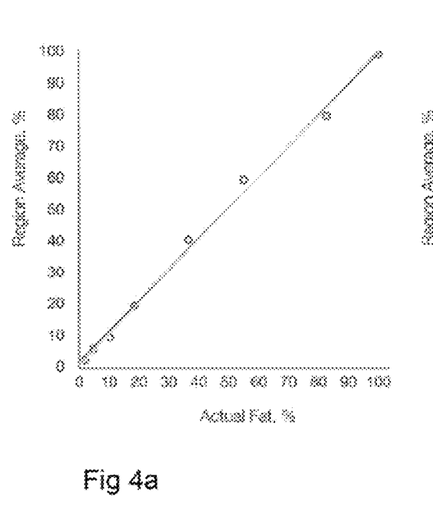
FIG. 4a shows a graph of an initial estimate of presence of fat in phantoms from an actual test of the present invention.
Figure 4B:
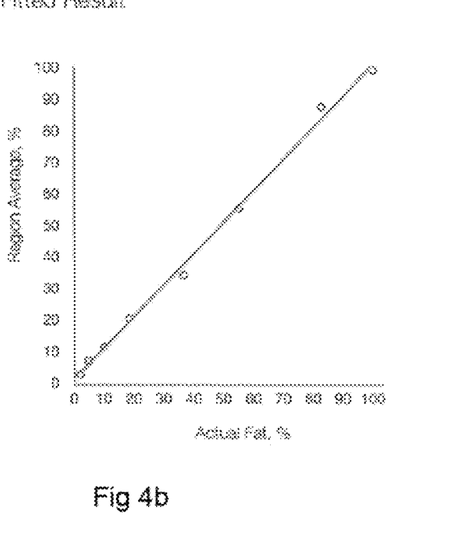
FIG. 4b shows a graph of fitted results using the initial estimates.

FIG. 4a gives an example as a graph of an initial estimate of % of fat compared to actual % fat. FIG. 4b is an example of a fitted result of % of fat compared to actual % fat.

FIG. 4b shows average fat percentages for each phantom region of interest plotted versus the labelled fat concentrations on the products. The embodiment of the present invention the basis for the results in FIG. 4b was accurate to within 0.2%, and precise to within 2.5%.

Figure 5A:
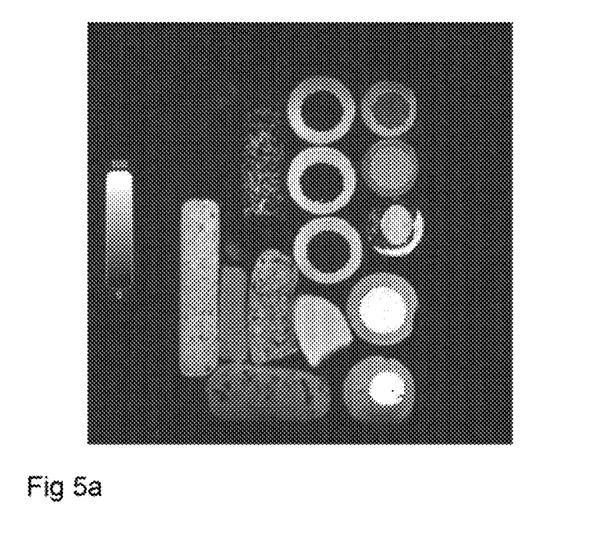
FIGS. 5a and 5b show percentage fat maps on phantoms imaged at 3.0 T within circular regions of interest, of the initial estimates realized by employing an embodiment of the present invention (FIG. 5b) and from fitted results using the initial estimates (FIG. 5a), respectively.
Figure 5B:
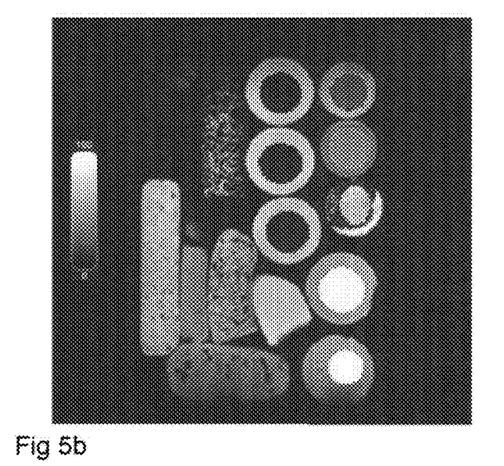

FIGS. 5a and 5b show percentage fat maps on phantoms imaged at 3.0 T within circular regions of interest, of the initial estimates realized by employing an embodiment of the present invention and front fitted results using the initial estimates, respectively.

One or more embodiments of the present invention enables estimation of the relative proportions of two dominant MR chemical species from magnitude gradient-echo image data, where one species has a multi-peak MR spectra that has two dominant peaks.

Although the description will predominantly refer to an MR signal volume comprising water and fat, the present invention can be applied to other MR chemical species, such as silicone.

In the case of water and silicone, their complex signals are predominantly in phase in multiples at ~220 Hz/T, which at a MR field strength of 1.5 T is in multiples of ~3.1 ms (based on a single characteristic MR frequency for silicone relative to water). The two main silicone hydrogen proton pools are predominantly in phase in multiples of ~26 Hz/T, which at a MR field strength of 1.5 T is in multiples of ~26.0 ms. Data for estimation of the relative proportions of silicone and water should thus ideally be collected out to ~26 ms at a field strength of 1.5 T, although data collected out to 75% of this value at ~19 ms can also be worked with for the present invention.

Figure 7:
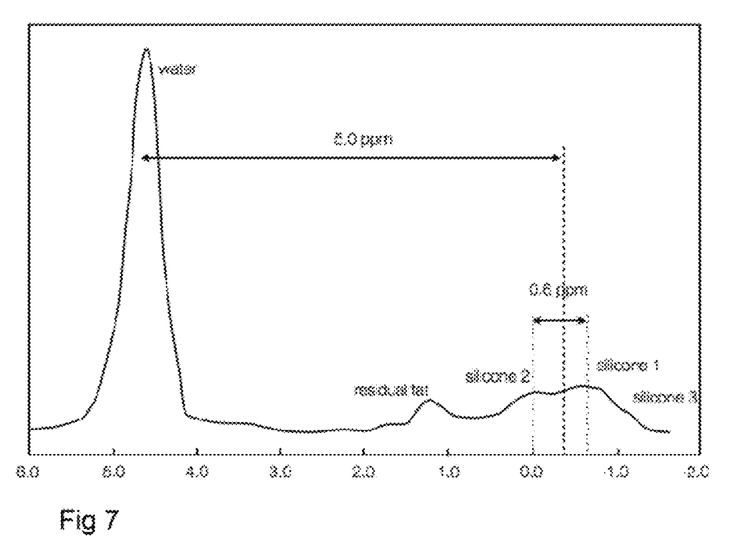
FIG. 7 shows a spectral diagram revealing the separation in peaks between water and silicone.

Referring to FIG. 7, a silicone MR spectrum is shown with multiple peaks 1-3, with the dominant (silicone 1) peak separated ~5.0 ppm from a dominant water peak. The silicone 2 secondary peak is separated ~0.6 ppm from the dominant silicone 1 peak. (A residual fat peak is left after near-total suppression of the fat signal).

The same pulse sequence can be used—a 2D spoiled gradient echo pulse sequence—in respect of silicone as for fat, but with the additional requirement that the images be acquired with fat suppression.

Thus, magnitude gradient echo image data can be acquired on phantoms and volunteers at 1.5 T and 3.0 T (Siemens Avanto and Philips Achieva, respectively) for silicone. A maximum scan time of 30 s can be used. In each case, a 2-D multi-echo spoiled gradient echo sequence (with fat suppression) is proposed with the following parameters: flip angle 20° and TR 200 ms to reduce T1-weighting; 16 equally spaced echo times per field strength of ~1.0 ms.T, slice thickness 8 mm; bandwidth of 500 Hz/pixel (at 1.5 T) and 1970 Hz/pixel (at 3.0 T); matrix size 256 pixels.

The amount of data collected out to the outer echo time for magnitude fitting of a combined silicone/water signal model should be in increments where the silicone and water signal go approximately in and out of phase, at half of 3.1 ms, which is every 1.55 ms at 1.5 T, such that up to 16 separate echo time images are collected out to 24.8 ms, or up to 12 echo time images are collected out to 18.6 ms (75% of 24.8 ms).

When imaging silicone, such as in breast implants, the fat signals can be suppressed so that the silicone signal is revealed as a bright image.

Gradient-echo image data is required to be collected out to echo times in the vicinity where either the complex signals from the two MR species are next in-phase after having first been out of phase, or to where the complex signals for the two dominant hydrogen proton pools of the species with a multi-peak spectra are next in phase having been first out of phase, whichever is the longer.

For water and fat, their complex signals are predominantly in phase in multiples at 140 Hz/T, which at a MR field strength of 1.5 T is in multiples of ~4.8 ms (based on a single characteristic MR frequency for fat relative to water). The two main fat hydrogen proton pools are predominantly in phase in multiples of 34 Hz/T, which at a MR field strength of 1.5 T is in multiples of ~19.6 ms. Data for estimation of the relative proportions of fat and water should thus ideally be collected out to 19.6 ms at a field strength of 1.5 T, although data collected out to ~75% of this value can also be worked with for the present invention.

The amount of data collected out to the outer echo time for magnitude fitting of a combined fat/water signal model should be in increments where the fat and water signal go approximately in and out of phase, at half of 4.8 ms, which is every 2.4 ms at 1.5 T, such that up to 8 separate echo time images are collected out to 19.6 ms, or up to 6 echo time images are collected out to 14.7 ms (75% of 19.6 ms).

Appropriately estimating the relative proportions of water and fat lies in splitting the data collected out to the longest echo time into two measurement time windows (which may 'overlap). The first measurement time window extends out from an echo time of 0 ms to the echo time point where the complex signals from the two dominant fat hydrogen proton pools are first out of phase, which is at half the echo time from where they are next in phase.

At a field strength of 1.5 T, the end point for the first measurement time window is then in the vicinity of half of 19.6 ms, at ~9.8 ms. The second measurement time window covers a span of echo times where the complex signal from the two dominant fat hydrogen proton pools are coming back in phase. This can be from the point at 9.8 ms out to 19.6 ms, or overlapping with the first window, from down to ~75% of these values, from ~7.3 ms out to ~14.7 ms.

The first measurement time window thus captures signal data up to where the two dominant hydrogen proton pools for fat go maximally out of phase (the "out-phase window"), whilst the second measurement time windows captures data where the complex signals from the two dominant hydrogen proton pools are coming back in phase (the "in-phase window").

Ideally, the out-phase and in-phase windows should thus span four different echo time images.

Over the out-phase and in-phase measurement windows, the deviation in signal intensities within a given signal volume relative to an overall reference relaxation process are determined. In this instance, the reference relaxation process is taken to be the average relaxation process for all hydrogen protons, described by a single exponential decay, although other signal model decay representations could be used. The reference relaxation process can modelled from the data by either curve fitting or other means of approximation, which may include empirical ones.

One empirical approach is to split the out-phase window in half into two sub-windows, and average the intensities and echo time values from the data in each window, and using the two derived intensity/echo time pairs from the two sub-windows, work out a 2 point approximation to the reference relaxation process according to the equation of single exponential decay.

Deviation in signal intensities relative to the reference relaxation process may be calculated in a number of ways. However, a preferred method is to subtract the reference signal intensity calculated from the reference relaxation equation at a given echo time from the actual signal intensity at that echo time, normalized relative to that actual signal intensity.

A list of deviations is thus obtained over the in-phase and out-phase windows that pair with the echo time images acquired.

Over each window, a characteristic deviation can then be determined, again in a number of ways, with a preferred method being the absolute value of the greatest deviation in a given window, which hereinafter will be referred to as the "in-phase deviation" for the in-phase window, and "out-phase deviation" for the out-phase window.

An initial estimate of the percentage fat fraction can be determined from the in-phase and out-phase deviations by, for example, a combination of scaling and thresholding.

With appropriate scaling of the out-phase deviation, the percentage fat fraction can be taken to be equal to the scaled out-phase deviation within empirically determined thresholds for the in-phase and out-phase deviations. Outside of these thresholds, the percentage fat fraction is no longer approximated by the scaled out-phase deviation, but is rather set to a scaling of one minus the scaled out-phase deviation.

One approach is to determine thresholds above which for the out-phase deviation and simultaneously below which for the in-phase deviation, the "outside of threshold" percentage fat approximation is preferred as a truer approximation of the actual percentage fat fraction than the "within threshold" percentage fat approximation.

With an initial estimate of the percentage fat fraction determined, initial estimates of the fat and water signal intensities at an echo time of 0 ms can be determined relative to the signal intensity at an echo time of 0 ms for the reference relaxation process.

The initial estimates for the relaxation rates of water and fat can also both be set relative to the relaxation rate of the reference relaxation process. These can be set as both being equal to the reference relaxation rate if the water/fat signal model is expressed as having a common relaxation rate for both water and fat.

Alternatively, if the water/fat signal model is expressed as having a different relaxation rate for water and fat, further empirical assumptions can be made to set different initial values for the relaxation rates of water and fat, such as fat having an inherently faster relaxation than water.

Refinements can also be made to the initial estimates for the water/fat signal model with different relaxation rates for water and fat, by first fitting a water/fat signal model with a common relaxation rate for water and fat to the magnitude image data. The fitted values can then be used as initial estimates for the water/fat signal model with different relaxation rates for water and fat, again applying an empirical criterion that the relaxation rate of fat is faster than that for water.

Figure 6A:
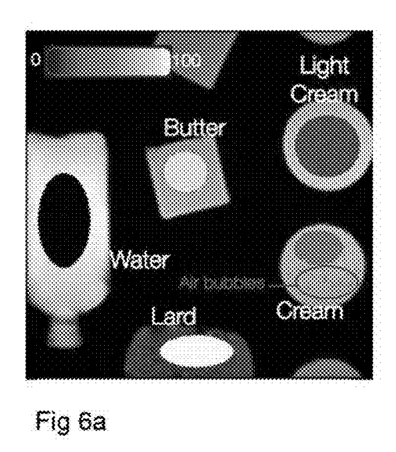
FIG. 6a shows an image of phantoms containing fat and imaged utilizing an embodiment of the present invention.

FIG. 6a shows an image of phantoms containing fat and imaged utilizing an embodiment of the present invention.

Figure 6B:
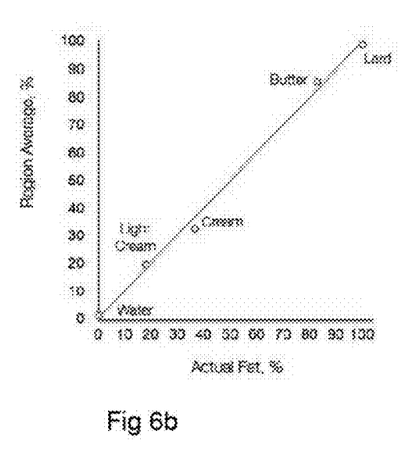
FIG. 6b shows a graph of Region Average % fat to Actual fat % with the % fat realized from the phantoms on an expected 1-to-1 line.

FIG. 6b shows a graph of Region Average % fat to Actual fat % with the % fat realized from the phantoms on to the expected 1-to-1 line.

I claim:

1. A method of characterising relative proportions of magnetic resonance (MR) chemical species where one or more of the chemical species has a multi-peak MR spectra from a magnetic resonance imaging system, the method comprising:
   a) defining an in-phase measurement time window and an out-phase measurement time window relative to a frequency difference between two dominant spectral peaks of at least one said multi-peak chemical species, where the in-phase window captures signal, from the magnetic resonance imaging system, that is progressing to being maximally in-phase for the two dominant peaks, and the out-phase window captures signal, from the magnetic resonance imaging system, that is progressing to being maximally out of phase for the two dominant peaks;
   b) identifying an increased upward deviation in the signal from the magnetic resonance imaging system over the in-phase window relative to a reference signal decay over the out-phase window, where such upward deviation in the signal from the magnetic resonance imaging system over the in-phase window provides an indicator of the increased presence of the one or more multi peak spectral species over the other species; and
   c) displaying to a user the relative proportions of the magnetic resonance chemical species determined from the indication of the upward deviation in the signal from the magnetic resonance imaging.

2. The method of claim 1, where deviation in the signal over the out-phase window is also identified relative to the reference signal decay over the out-phase window, where said out-phase deviation acts as an indicator of the reduced presence of the one or more multi-peak spectral species relative to the other species.

3. The method of claim 2, wherein the method is utilized in magnetic resonance imaging (MRI).

4. The method of claim 1, wherein the multi-peak chemical species is fat or silicone.

5. The method of claim 3, further comprising MR imaging a proportion and/or distribution of fat in a body.

6. The method of claim 1, where the reference signal decay is averaged from the relaxation effects of the chemical species contributing to the MR signal.

7. The method of claim 1, where the reference signal decay is a single exponential decay representing averaging of the relaxation effects of the chemical species contributing to the MR signal.

8. The method of claim 1, further comprising determining the reference signal decay by an empirical approach including the steps of:
   fractioning the out-phase window into two smaller windows;
   determining an average intensity value and an average measurement time value in each of the smaller windows; and
   using the two average intensity/measurement time pairs to determine a 2-point approximation for a reference relaxation process according to an equation of single exponential decay.

9. The method of claim 1, further comprising determining a deviation in signal intensity from the reference signal decay by subtracting a reference signal intensity calculated from a reference relaxation equation at a given measurement time from an actual signal intensity at that measurement time, normalised relative to that actual signal intensity.

10. The method of claim 9, further comprising determining a characteristic in-phase or out-phase deviation from the in-phase or an out-phase deviation, respectively.

11. The method of claim 9, further comprising determining a characteristic in-phase or out-phase deviation as a greatest absolute deviation over the in-phase or out-phase window, respectively.

12. The method of claim 9, further comprising determining the proportion of a multi-peak chemical species by a combination of scaling and thresholding of the in-phase and an out-phase deviation.

13. The method of claim 9, where a lesser proportion of the multi-peak chemical species relative to the other species is taken to be equal to a scaled out-phase deviation within empirically determined thresholds for the in-phase and an out-phase deviation.

14. The method of claim 9, where a greater proportion of the multi-peak chemical species relative to the other species is taken to be equal to a scaling of one minus a scaled out-phase deviation outside of empirically determined thresholds for the in-phase and an out-phase deviation.

15. The method of claim 12, further comprising using the proportion of the multi-peak chemical species to determine initial estimates of the signal intensities of the chemical species at a zero measurement time with reference to the signal intensity at a zero measurement time from the reference signal decay.

16. The method of claim 1, further comprising characterising magnetic resonance (MR) relaxation rates and relative proportions of the two or more magnetic resonant chemical species, where one said chemical species has two or more dominant MR spectral peaks relative to the other said chemical species that has one dominant MR spectral peak.

17. The method of claim 16, wherein the chemical species with two or more dominant spectral peaks is fat and the chemical species with one dominant spectral peak is water.

18. The method of claim 1, further comprising estimating a percentage or proportion of fat fraction, and further comprising accounting for one or more additional confounds from collected echo time image data.

19. The method of claim 18, wherein the one or more additional confounds includes R2* enhancement.

20. The method of claim 1, further comprising collecting gradient-echo image data out to echo times where either complex signals from the two chemical species are next in-phase after having first been out of phase, or to where complex signals for two dominant hydrogen proton pools of the species with a multi-peak spectra are next in phase having been first out of phase, whichever is the longer.

21. The method of claim 1, further comprising estimating the relative proportions of the two or more chemical species by separating collected data out to a longest echo time into two measurement time windows.

22. The method of claim 21, wherein a first measurement time window extends out from an echo time of 0 milliseconds (0 ms) to an echo time point where complex signals from two dominant fat hydrogen proton pools are first out of phase.

23. The method of claim 21, wherein a second measurement time window covers a span of echo times where complex signals from two dominant fat hydrogen proton pools are coming back in phase.

* * * * *